US008044071B2

(12) United States Patent
Carroll

(10) Patent No.: US 8,044,071 B2
(45) Date of Patent: Oct. 25, 2011

(54) METHOD FOR REDUCING SIDE EFFECTS OF $CB_2$ RECEPTOR AGONIST THERAPY USING A COMBINATION OF A SELECTIVE $CB_2$ RECEPTOR AGONIST AND A SELECTIVE $CB_1$ RECEPTOR ANTAGONIST

(75) Inventor: William A. Carroll, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/252,811

(22) Filed: Oct. 16, 2008

(65) Prior Publication Data

US 2009/0105304 A1 Apr. 23, 2009

Related U.S. Application Data

(60) Provisional application No. 60/980,967, filed on Oct. 18, 2007.

(51) Int. Cl.
*A61K 31/4453* (2006.01)
*A61K 31/426* (2006.01)

(52) U.S. Cl. ........................................ 514/326; 514/371

(58) Field of Classification Search ........................ None
See application file for complete search history.

(56) References Cited

U.S. PATENT DOCUMENTS 7,875,640 B2 1/2011 Kolasa et al.
2008/0139635 A1 6/2008 Martin et al.

FOREIGN PATENT DOCUMENTS

EP 1820504 A1 8/2007
WO WO2006051704 A1 5/2006
WO WO-2008121558 A1 10/2008

OTHER PUBLICATIONS

Dellemijn et al., Lancet, 349(9054), (Mar. 15, 1997),pp. 753-758 (Abstract).*
Malan et al., Chemistry and Physics of Lipids, (Dec. 2002), 121(1-2), 191-200.*
Arevalo-Martin, A., et al., "Therapeutic Action of Cannabinoids in a Murine Model of Multiple Sclerosis," Journal of Neuroscience, 2003, 2511-2516, vol. 23, No. 7.
Benito, C, et al., "A Glial Endogenous Cannabinoid System Is Upregulated in the Brains of Macaques with Simian Immunodeficiency Virus-Induced Encephalitis," Journal of Neuroscience, 2005, 2530-2536, vol. 25—Issue 10.
Benito, C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, 11136-11141, vol. 23—Issue 35.
Brennan, T.J. et al., "Characterization of a rat model of incisional pain," (Binary/Image), 1996, 493-501, vol. 64.
Buckley, N.E. et al., "Immunomodulation by cannabinoids is absent in mice deficient for the cannabinoid CB receptor," European Journal of Pharmacology, 2000, 141-149, vol. 396.
Carlisle, S.J. et al., "Differential expression of the CB2 cannabinoid receptor by rodent macrophages and macrophage-like cells in relation to cell activation," International Immunopharmacology, 2002, 69, vol. 2.
Carrier, E.J. et al., "Endocannabinoids in Neuroimmunology and Stress," Current Drug Targets—CNS & Neurological Disorders, 2005, 657-665, vol. 4.
Casanova, M.L. et al., "Inhibition of skin tumor growth and angiogenesis in vivo by activation of cannabinoid receptors," Journal of Clinical Investigation, 2003, 43-50, vol. 111.
Chaplan, S.R. et al., "Quantitative assessment of tactile allodynia in the rat paw," Journal of Neuroscience Methods, 1994, 55-63, vol. 53.
Clayton, N. et al., "CB1 and CB2 cannabinoid receptors are implicated in inflammatory pain," (Binary/Image), 2002, 253-260, vol. 96.
Galiégue, et al., "Expression of central and peripheral cannabinoid receptors in human immune tissues and leukocyte subpopulations," European Journal of Biochemistry, 1995, 54-61, vol. 232.
Golech, S.A. et al., "Human brain endothelium: coexpression and function of vannilloid and endocannabinoid receptors," Molecular Brain Research, 2004, 87-92, vol. 132.
Hanus, L. et al., "HU-308: A specific agonist for CB 2, a peripheral cannabinoid receptor," Proceedings of the National Academy of Science, 1999, 14228-14233, vol. 96.
Hohmann, A.G. et al., "Selective Activation of Cannabinoid CB2 Receptors Suppresses Hyperalgesia Evoked by Intradermal Capsaicin," Journal of Pharmacology and Experimental Therapeutics, 2004, 446-453, vol. 308.
Ibrahim, M.M. et al., "Activation of CB2 cannabinoid receptors by AM1241 inhibits experimental neuropathic pain: Pain inhibition by receptors not present in the CNS," Proceedings of the National Academy of Science, 2003, 10529-10533, vol. 100—Issue 18.
Ibrahim, M.M. et al., "CB2 cannabinoid receptor activation produces antinociception by stimulating peripheral release of endogenous opioids," Proceedings of the National Academy of Science, 2005, 3093-3098, vol. 102—Issue 8.
International Search Report for application No. PCT/US08/080253, Mailed on Mar. 3, 2009, 3 pages.
Jhaveri M D et al., "Cannabinoid CB2 receptor-mediated antinociception in models of acute and chronic pain," Molecular Neurobiology, 36 (1) , 26-35.
Julien, B, et al., "Antifibrogenic Role of the Cannabinoid Receptor CB2 in the Liver," Gastroenterology, 2005, 742-755, vol. 128.
Kim, S.H. & Chung, J.M. "An experimental model for peripheral neuropathy produced by segmental spinal nerve ligation in the rat," (Binary/Image), 1992, 355-363, vol. 50—Issue 3.
Kreutzberg, G W "Microglia: a sensor for pathological events in the CNS," Trends in Neuroscience, 1996, 312-318, vol. 19.
Lotersztajn, S. et al., "Hepatic Fibrosis: Molecular Mechanisms and Drug Targets," Annual Review of Pharmacology and Toxicology, 2005, 605-628, vol. 45.
MacLennan S.J. et al., "Evidence for inverse agonism of SR141716A at human recombinant cannabinoid CB1 and CB2 receptors," Br J Pharmacol, 1998, vol. 124 (4), pp. 619-622.
Malan, T.P. et al., "CB2 cannabinoid receptor-mediated peripheral antinociception," (Binary/Image), 2001, 239-245, vol. 93.

(Continued)

*Primary Examiner* — Phyllis G. Spivack

(74) *Attorney, Agent, or Firm* — Nancy J. Gettel; Sonali Srivastava; Andrew M. Parial

(57) ABSTRACT

The present application describes a method of treating pain with a combination of a $CB_2$ cannabinoid receptor agonist and rimonabast.

5 Claims, 8 Drawing Sheets

OTHER PUBLICATIONS

Maresz, K, et al., "Modulation of the cannabinoid CB2 receptor in microglial cells in response to inflammatory stimuli," Journal of Neurochemistry, 2005, 437-445, vol. 95.
Mathison, R, et al., "Effects of cannabinoid receptor-2 activation on accelerated gastrointestinal transit in lipopolysaccharide-treated rats," British Journal of Pharmacology, 2004, 1247-1254, vol. 142.
McKallip, R.J. et al., "Targeting CB2 cannabinoid receptors as a novel therapy to treat malignant lymphoblastic disease," (Binary/Image), 2002, 627-634, vol. 15—Issue 2.
Molina-Holgado, F. et al., "Endogenous Interleukin-1 Receptor Antagonist Mediates Anti-Inflammatory and Neuroprotective Actions of Cannabinoids in Neurons and Glia," Journal of Neuroscience, 2003, 6470-6474, vol. 23—Issue 16.
Mukherjee S., Adams M., Whiteaker K., et al., "Species comparison and pharmacological characterization of rat and human CB2 cannabinoid receptors.," Eur J Pharmacol, 2004, vol. 505, pp. 1-9.
Nackley, A.G. et al., "Selective activation of cannabinoid CB2 receptors suppresses spinal fos protein expression and pain behavior in a rat model of inflammation," Neuroscience, 2003, 747-757, vol. 119.
Ni, X. et al., "Win 55212-2, a cannabinoid receptor agonist, attenuates leukocyte/endothelial interactions in an experimental autoimmune encephalomyelitis model," Multiple Sclerosis, 2004, 158-164, vol. 10.
Nunez, E. et al., "Cannabinoid CB2 Receptors Are Expressed by Perivascular Microglial Cells in the Human Brain: An Immunohistochemical Study," Synapse, 2004, 208-213, vol. 53.
Patel, J.J. et al., "Inhibition of guinea-pig and human sensory nerve activity and the cough reflex in guinea-pigs by cannabinoid (CB2) receptor activation," British Journal of Pharmacology, 2003, 261-268, vol. 140.
Pertwee, R.G. "Cannabinoids and multiple sclerosis," Pharmacology & Therapeutics, 2002, 165-174, vol. 95.
Quartilho, A. et al., "Inhibition of Inflammatory Hyperalgesia by Activation of Peripheral CB2 Cannabinoid Receptors," Anesthesiology, 2003, 955-960, vol. 99.
Ramirez, B.G. et al., "Prevention of Alzheimer's Disease Pathology by Cannabinoids: Neuroprotection Mediated by Blockade of Microglial Activation," Journal of Neuroscience, 2005, 1904-1913, vol. 25—Issue 8.
Sanchez C. et al., "Inhibition of Glioma Growth in Vivo by Selective Activation of the CB2 Cannabinoid Receptor1," Cancer Research, 2001, 5784-5789, vol. 61.
Steffens S. et al., "Low dose oral cannabinoid therapy reduces progression of atherosclerosis in mice," (Binary/Image), 2005, 782-786, vol. 434.
Valenzano K.J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, 658-672, vol. 48.
Walter L. et al., "Cannabinoids and neuroinflammation," Pharmacology, 2004, 775-785, vol. 141.
Warhurst A.C. et al., "Interferon ? induces differential upregulation of a and β chemokine secretion in colonic epithelial cell lines," (Binary/Image), 1998, 208-213, vol. 42.
Watkins L.R. et al, "Glial activation: a driving force for pathological pain," Trends in Neuroscience, 2001, 450-455, vol. 24—Issue 8.
Whiteside G T et al., "The role of the cannabinoid CB2 receptor in pain transmission and therapeutic potential of small molecule CB2 receptor agonists," Current Medicinal Chemistry, 14 (8), 917-936, p. 928, 2007.
Williams K. et al., "Central nervous system perivascular cells are immunoregulatory cells that connect the CNS with the peripheral immune system," (Binary/Image), 2001, 156-164, vol. 36.
Wright K. et al., "Differential Expression of Cannabinoid Receptors in the Human Colon: Cannabinoids Promote Epithelial Wound Healing," Gastroenterology, 2005, 437-453, vol. 129.
Yao B.B et al., "In vitro pharmacological characterization of AM1241: a protean agonist at the cannabinoid CB2 receptor?," Br J Pharmacol, 2006, vol. 149 (2), pp. 145-154.
Yoshihara S. et al., "Cannabinoid Receptor Agonists Inhibit Sensory Nerve Activation in Guinea Pig Airways", American Journal of Respiratory and Critical Care Medicine, 2004, 941-946, vol. 170.
Yoshihara S. et al., "Endogenous Cannabinoid Receptor Agonists Inhibit Neurogenic Inflammations in Guinea Pig Airways" Allergy and Immunology, 2005, 80-87, vol. 138.
Yoshihara S. et al., "The Cannabinoid Receptor Agonist WIN 55212-2 Inhibits Neurogenic Inflammations in Airway Tissues," Journal of Pharmacological Sciences, 2005, 77-82, vol. 98—Issue 1.
Zimmer, A et al., "Increased mortality, hypoactivity, and hypoalgesia in cannabinoid CB1 receptor knockout mice," Proceedings of the National Academy of Science, 1999, 5780-5785, vol. 96.
Jhaveri M D et al., "Cannabinoid CB2 receptor-mediated antinociception in models of acute and chronic pain," Molecular Neurobiology, 36 (1) , 26-35, (2007).
Berge, et al., "Pharmaceutical Salts," Journal of Pharmaceutical Sciences, 1977, vol. 66 (1), pp. 1-19.
Bouchard, et al., "Contribution of Endocannabinoids in the Endothelial Protection Afforded by Ischemic Preconditioning in the Isolated Rat Heart," Life Sciences, 2003, vol. 72 (16), pp. 1859-1870.
Boyle, et al., "Osteoclast Differentiation and Activation," Nature, 2003, vol. 423 (6937), pp. 337-342.
Cichewicz, D., "Synergistic Interactions Between Cannabinoid and Opioid Analgesics," Life Sciences, 2004, vol. 74 (11), pp. 1317-1324.
Clayton, N. et al., "CB1 and CB2 cannabinoid receptors are implicated in inflammatory pain," (Binary/Image), 2002, 253-260, vol. 96.
Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Dellemijn, et al., "Randomized double-blind active-placebo-controlled crossover trial of intravenous fentanyl in neuropathic pain," Lancet, 1997, vol. 349 (9054), pp. 753-758.
Dixon, W., "Efficient Analysis of Experimental Observations," Annual Review of Pharmacology and Toxicology, 1980, vol. 20, pp. 441-462.
Filippo, et al., "Cannabinoid CB2 Receptor Activation Reduces Mouse Myocardial Ischemia-Reperfusion Injury: Involvement of Cytokine/Chemokines and PMN," Journal of Leukocyte Biology, 2004, vol. 75 (3), pp. 453-459.
Galiegue, et al., "Expression of central and peripheral cannabinoid receptors in human immune tissues and leukocyte subpopulations," European Journal of Biochemistry, 1995, 54-61, vol. 232.
Greene, et al., "Protection for the Amino group," Protective Groups in Organic Synthesis, 1999, Third Edition, pp. 494-653.
Golech, S.A. et al., "Human brain endothelium: coexpression and function of vannilloid and endocannabinoid receptors," Molecular Brain Research, 2004, 87-92, vol. 132.
Grotenhermen, et al., "IACM 2nd Conference on Cannabinoids in Medicine," Expert Opinion in Pharmacotherapy, 2003, vol. 4 (12), pp. 2367-2371.
Hanus, L. et al., "HU-308: A specific agonist for CB 2, a peripheral cannabinoid receptor," Proceedings of the National Academy of Science, 1999, 14228-14233, vol. 96.
Hohmann, A.G. et al., "Selective Activation of Cannabinoid CB2 Receptors Suppresses Hyperalgesia Evoked by Intradermal Capsaicin," Journal of Pharmacology and Experimental Therapeutics, 2004, 446-453, vol. 308.
Ibrahim, M.M. et al., "Activation of CB2 cannabinoid receptors by AM1241 inhibits experimental neuropathic pain: Pain inhibition by receptors not present in the CNS," Proceedings of the National Academy of Science, 2003, 10529-10533, vol. 100-Issue 18.
Ibrahim, M.M. et al., "CB2 cannabinoid receptor activation produces antinociception by stimulating peripheral release of endogenous opioids," Proceedings of the National Academy of Science, 2005, 3093-3098, vol. 102-Issue 8.
Ihenetu, et al., "Inhibition of Interleukin-8 Release in the Human Colonic Epithelial Cell Line HT-29 by Cannabinoids," European Journal of Pharmacology, 2003, vol. 458 (1-2), pp. 207-215.

International Search Report for Application No. PCT/US08/057460, mailed on Aug. 20, 2008, 3 pages.
International Search Report for application No. PCT/US08/080253, Mailed on Mar. 3, 2009, 3 pages.
Joshi, et al., "Comparison of Antinociceptive Actoins of Standard Analgesics in Attenuating Capsaicin and Nerve-Injury-Induced Mechanical Hypersensitivity," Neuroscience, 2006, vol. 143, pp. 587-596.
Julien, B, et al., "Antifibrogenic Role of the Cannabinoid Receptor CB2 in the Liver," Gastroenterology, 2005, 742-755, vol. 128.
Karsak, et al., "Cannabinoid Receptor Type 2 Gene is Associated with Human Osteoporosis," Human Molecular Genetics, 2005, vol. 14 (22), pp. 3389-3396.
Kim, S.H. & Chung, J.M. "An experimental model for peripheral neuropathy produced by segmental spinal nerve ligation in the rat," (Binary/Image), 1992, 355-363, vol. 50-Issue 3.
Kreutzberg, G W "Microglia: a sensor for pathological events in the CNS," Trends in Neuroscience, 1996, 312-318, vol. 19.
Lepicier, et al., "Endocannabinoids Protect the Rat Isolated Heart Against Ischaemia," British Journal of Pharmacology, 2003, vol. 139, pp. 805-815.
Li, et al., "An Improved Synthesis of Pyran-3,5-Dione: Application to the Synthesis of Abt-598, A Potassium Channel Opener, Via Hantzsch Reaction," Journal of Organic Chemistry, 2006, vol. 71 (4), pp. 1725-1727.
Malan, et al., "Inhibition of pain responses by activation of CB(2) cannabinoid receptors," Chemistry and Physics of Lipids, 2002, vol. 121 (1-2), pp. 191-200.
Mallat, et al., "Cannabinoid Receptors as new Targets of Antifibrosing Strategiesduring Chronic Liver Diseases," Expert Opinion on Therapeutic Targets, 2007, vol. 11 (3), pp. 403-409.
Poste, et al., "Lipid Vesicles as Carriers for Introducing Biologically Active Materials into Cells," Methods in Cell Biology, 1976, vol. 14, pp. 33-71.

* cited by examiner

METHOD FOR REDUCING SIDE EFFECTS OF $CB_2$ RECEPTOR AGONIST THERAPY USING A COMBINATION OF A SELECTIVE $CB_2$ RECEPTOR AGONIST AND A SELECTIVE $CB_1$ RECEPTOR ANTAGONIST

Present invention seeks priority from U.S. Provisional Patent Application 60/980,967, filed on Oct. 18, 2007, which is incorporated herein by reference in its entirety.

TECHNICAL FIELD AND BACKGROUND

The present application relates to a method of treating pain states with reduced side effects resulting from a therapeutic use of a $CB_2$ cannabinoid receptor agonist comprising a combination therapy consisting of a $CB_2$ cannabinoid receptor agonist in an amount effective to obtain a therapeutic effect, and a $CB_1$ cannabinoid receptor ligand to the subject in an amount effective to block the adverse effects but not to antagonize the therapeutic effect of the cannabinoid receptor agonist.

(−)-$\Delta^9$-Tetrahydrocannabinol ($\Delta^9$-THC), the major psychoactive constituent of marijuana, exerts a broad range of biological effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. Activation of the $CB_1$ receptor by administration of a $CB_1$ agonist produces a number of undesirable physiological and behavioral effects. In the central nervous system, activation of the $CB_1$ receptor can result in a variety of psychotropic effects such as euphoria, sedation, catalepsy, paranoia, panic and anxiety. $CB_1$ activation also negatively impacts cognitive function, leading to a loss of short-term memory, poor executive function and impaired learning. $CB_1$ activation also produces physiological effects that manifest themselves outside the central nervous system such as hypothermia, increased heart rate, decreased blood pressure, and dry mouth. The undesirable effects mediated by CB1 activation may negatively impact the usefulness to a patient of any medication that displays some ability to activate the CB1 receptor. The undesirable effects resulting from activation of the $CB_1$ receptor with a $CB_1$ agonist may be blocked, inhibited, or prevented by administration of a selective $CB_1$ antagonist or inverse agonist.

Several lines of evidence support the assertion that $CB_2$ receptors play a role in analgesia. For example, Zimmer et al. have reported that the nonselective cannabinoid agonist $\Delta^9$-THC retains some analgesic efficacy in $CB_1$ receptor knockout mice (Zimmer, A., et al., Proc. Nat. Acad. Sci., 1999, 96, 5780-5785). HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabiniod ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260). The analgesic effects induced by these $CB_2$-selective ligands are blocked by $CB_2$ and not by $CB_1$ receptor antagonists.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ agonists may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. They are quiescent and resting having a ramified morphology as long as the CNS is healthy. Microglia express a variety of receptors enabling them to survey the CNS and respond to pathological events. Insult or injury to the CNS leads to microglial cell activation, which is characterized by various morphological changes allowing response to the lesion. Ramifications are retracted and microglia are transformed into amoeboid-like cells with phagocytic function. They can proliferate, rapidly migrate to the site of injury, and produce and release cytokines, chemokines and complement components (Watkins L. R., et al., Trends in Neuroscience, 2001, 24(8), 450; Kreutzberg, G. W., Trends Neurosci., 1996, 19, 312-318). $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. It is conceivable that $CB_2$ receptors may be more susceptible to pharmacological effects during neuroinflammation (Walter, L., Stella, N., Br. J. Pharmacol. 2004, 141, 775-785). Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

$CB_2$ receptor expression has been detected in perivascular microglial cells within normal, healthy human cerebellum (Nunez, E., et al., Synapse, 2004, 58, 208-213). Perivascular cells are immunoregulatory cells located adjacent to CNS blood vessels and, along with parenchymal microglia and astrocytes, they play a pivotal role in maintaining CNS homeostasis and blood-brain barrier functionality (Williams, K., et al., Glia, 2001, 36, 156-164). $CB_2$ receptor expression has also been detected on cerebromicrovascular endothelial cells, which represent a main component of the blood-brain barrier (Golech, S. A., et al., Mol. Brain. Res., 2004, 132, 87-92). A recent report demonstrated that $CB_2$ receptor expression is up-regulated in the brains of macaques with simian immunodeficiency virus-induced encephalitis (Benito, C., et al., J. Neurosci. 2005, 25(10), 2530-2536). Thus, compounds that affect $CB_2$ signaling may protect the blood-brain barrier and be clinically useful in the treatment of neuroinflammation and a variety of neuroinflammatory disorders including retroviral encephalitis, which occurs with human immunodeficiency virus (HIV) infection in the CNS.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor agonists may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ agonists possessing both anti-inflammatory and neuroprotective actions thus may have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor agonists represents a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor agonists represents a unique approach for the treatment of liver fibrosis.

$CB_2$ receptors are involved in the neuroprotective and anti-inflammatory mechanisms induced by the interleukin-1 receptor antagonist (IL-1ra) (Molina-Holgado, F., et al., J. Neurosci., 2003, 23(16), 6470-6474). IL-1ra is an important anti-inflammatory cytokine that protects against ischemic, excitotoxic, and traumatic brain insults. $CB_2$ receptors play a role in mediating these neuroprotective effects indicating that $CB_2$ agonists may be useful in the treatment of traumatic brain injury, stroke, and in mitigating brain damage.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective agonists may have utility as antitussive agents for the treatment of pulmonary inflammation, chronic cough, and a variety of airway inflammatory diseases including but not limited to asthma, chronic obstructive pulmonary disease, and pulmonary fibrosis.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atherosclerosis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ agonists may have utility as anticancer agents against tumors of immune origin.

In view of this evidence, compounds that are selective agonists for the CB2 receptor over the $CB_1$ receptor are potential therapeutic agents for the treatment of a variety of disorders including inflammatory pain, inflammatory disorders, immune disorders, neurological disorders, neurodegeneration, cancer, respiratory disorders, cardiovascular disorders, osteoporosis, obesity, and diabetes.

Pain alleviation occurs at doses of a $CB_2$ selective agonist that do not cause or may to a very limited extent cause undesirable effects associated with $CB_1$ receptor activation. At higher doses, however, drug concentrations of a $CB_2$ selective agonist may reach sufficiently high levels so as to begin to activate $CB_1$ receptors, due to some residual weak $CB_1$ activity of the $CB_2$ selective agent producing ataxia and catalepsy (Valenzano et al., Neuropharmacology, Vol. 48 pages 658-672, 2005). Therefore, at higher doses $CB_2$ selective agonists may begin to display the aforementioned undesirable effects due to residual $CB_1$ activation.

In view of the aforementioned evidence, a combination therapy co-administering a $CB_2$ selective agonist and a $CB_1$ selective antagonist or inverse agonist can provide the therapeutic benefit of alleviating pain through activation of $CB_2$ receptors while concomitantly preventing the undesirable adverse effects due to the residual weak activation of the $CB_1$ receptor. This combination therapy provides a safer, more tolerable and more effective method of treating pain, or any other disorder mediated through $CB_2$ receptors, with reduced incidence of abuse liability.

DETAILED DESCRIPTION OF THE INVENTION

Figure 1A:
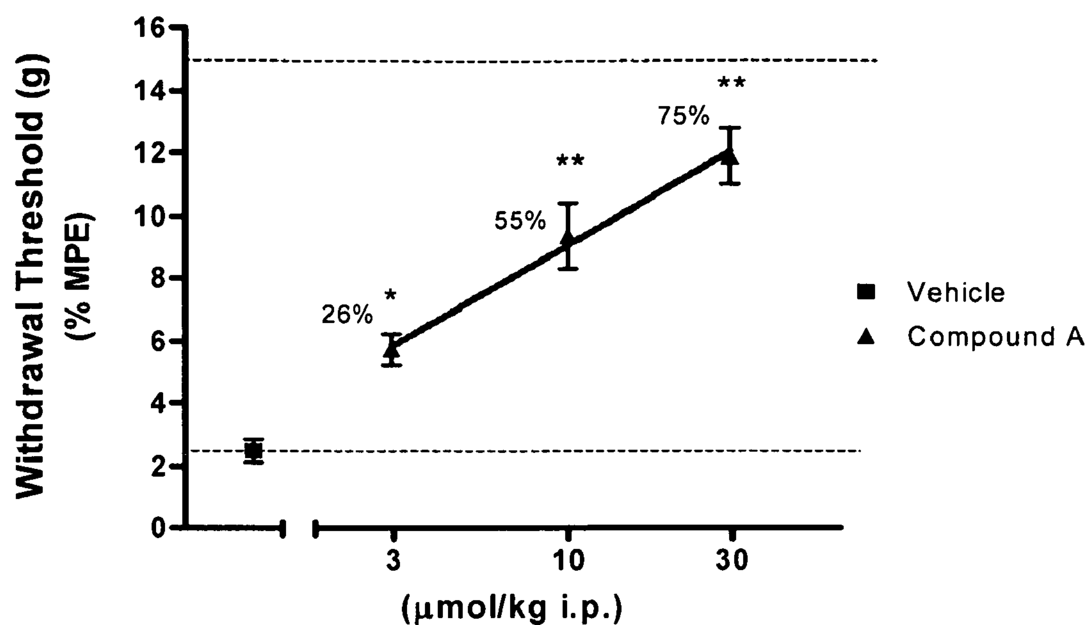
FIG. 1A shows the effect of (Z)—N-(5-tert-butyl-3-butylthiazol-2(3H)-ylidene)-5-chloro-2-methoxybenzamide, a $CB_2$ selective agonist, in skin incision pain model.

The present application claims a method for treating a subject suffering from a condition treatable with a $CB_2$ selective receptor agonist using a combination therapy comprising administering a $CB_2$ receptor agonist in an amount effective to obtain a therapeutic effect, and a $CB_1$ receptor ligand to the subject in an amount effective to block any $CB_1$ mediated adverse effects but not to antagonize the therapeutic effect of the $CB_2$ selective receptor agonist. It is intended that the selective $CB_1$ cannabinoid receptor ligand may be a $CB_1$ receptor antagonist, or a $CB_1$ receptor inverse agonist. It is also intended that the combination therapy comprising the $CB_2$ cannabinoid receptor agonist and the $CB_1$ receptor ligand, may be represented by the separate administration of a pharmaceutical composition containing the selective $CB_2$ cannabinoid receptor agonist, and a pharmaceutical composition containing the $CB_1$ receptor ligand, each pharmaceutical composition further comprising a therapeutically acceptable carrier. On the other hand, the combination therapy comprising the $CB_2$ cannabinoid receptor agonist and the $CB_1$ receptor ligand, may be represented by a single pharmaceutical composition comprising both compounds and therapeutically acceptable carrier, in which the $CB_1$ receptor ligand may be a $CB_1$ receptor antagonist, or a $CB_1$ receptor inverse agonist.

The present invention also relates to a method of reducing the side and unwanted effects of a $CB_2$ receptor agonist in a subject suffering from a condition treatable with a $CB_2$ receptor agonist, comprising administering a selective $CB_2$ receptor agonist and administering a $CB_1$ receptor ligand to the subject in an amount effective to block the side and unwanted effects but not to antagonize the therapeutic effect of the $CB_2$ receptor agonist. It is intended that the selective $CB_1$ receptor ligand may be a $CB_1$ receptor antagonist, or a $CB_1$ receptor inverse agonist.

Conditions treatable with the combination therapy of the invention, comprising administration of a CB2 selective agonist and a CB1 selective ligand (antagonist or inverse agonist), include pain, specifically neuropathic pain, nociceptive pain, or inflammatory pain. Other treatable conditions of the present invention include but are not limited to inflammatory disorders, immune disorders, neurological disorders, cancer of the immune system, respiratory disorders, obesity, diabetes, and cardiovascular disorders. Evidence to support said claim is present herein.

Several lines of evidence support the assertion that $CB_2$ receptors are associated with a variety of cells and tissues, and having a role in many physiological mechanisms that make selective agonists of the $CB_2$ receptor important therapeutic agents for a large variety of disorders.

The analgesic effects induced by selective $CB_2$ agonists are blocked by $CB_2$ and not by $CB_1$ receptor antagonists. $CB_2$ agonists are useful in the treatment of pain states comprising neuropathic pain, inflammatory pain or nociceptive pain, arising from disorders such as cancer, HIV, multiple sclerosis, diabetic neuropathy, post-herpetic neuralgia, arthritis, osteoarthritis, rheumatoid arthritis, surgical procedures and others. Some residual $CB_1$ receptor activation may induce unwanted side effects such as ataxia, catalepsy, and euphoria. Administration or combination of a selective $CB_2$ receptor agonist with a selective $CB_1$ receptor antagonist/inverse agonist provides a way to induce analgesia without the liability of the undesired side effects, which include tolerance, dependence, addiction, sedation, euphoria, dysphoria, memory impairment, hallucination, depression, dry mouth, increased heart rate, dizziness and headache among others.

$CB_1$ selective antagonist and inverse agonist molecules are well-known to those skilled in the art. Examples of representative $CB_1$ selective antagonists and inverse agonists can be found in the following literature references: Muccioli, *Expert Opin. Ther. Pat.* (2006) 16, pp 1405-1423; Barth, *Ann. Rep. Med. Chem.* (2005), 40, pp 103-118; Hertzog, *Expert Opin. Ther. Pat.* (2004) 14, pp 1435-1452. The examples contained within the foregoing citations are meant to be illustrative of $CB_1$ selective antagonists and inverse agonists and do not limit the scope of $CB_1$ selective antagonists and inverse agonists contemplated as part of the invention.

Rimonabant, also known as SR141716A and 5-(4-chlorophenyl)-1-(2,4-dichlorophenyl)-4-methyl-N-(piperidin-1-yl)-1H-pyrazole-3-carboxamide, is a particular $CB_1$ antagonist/inverse agonist contemplated as part of the invention.

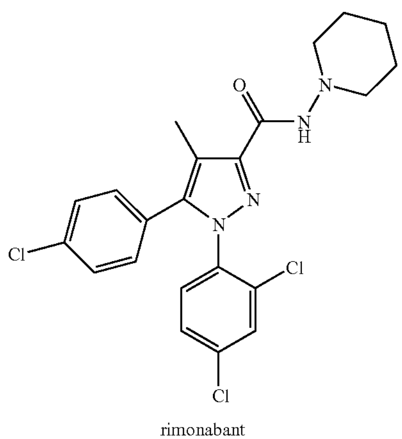

rimonabant

Taranabant, also known as MK-0364 and N-[(1S,2S)-3-(4-chlorophenyl)-2-(3-cyanophenyl)-1-methylpropyl]-2-methyl-2-{[5-(trifluoromethyl)pyridin-2-yl]oxy}propanamide is a particular $CB_1$ antagonist/inverse agonist contemplated as part of the invention.

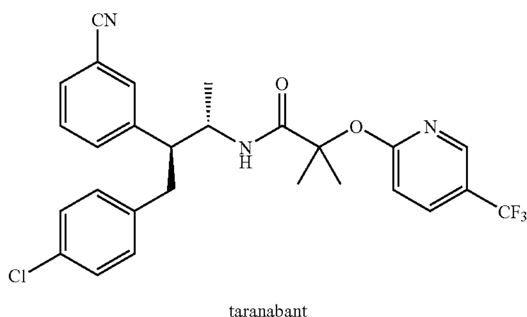

taranabant $CB_2$ agonist molecules are well-known to those skilled in the art. Examples of representative $CB_2$ agonists can be found in the following literature reference: Cheng, *Expert Opin. Invest. Drugs Vol.* 16, pages 951-965 (2007). For the purpose of the present invention, examples of such $CB_2$ selective agonists that are known in the scientific literature include but are not limited to AM1241, HU308, JWH-133, GW405833, (Z)—N-(5-tert-butyl-3-butylthiazol-2(3H)-ylidene)-5-chloro-2-methoxybenzamide, and (Z)—N-(3-(2-methoxyethyl)-4,5-dimethylthiazol-2(3H)-ylidene)-2,2,3,3-tetramethylcyclopropanecarboxamide. The foregoing examples are meant to be illustrative of $CB_2$ selective agonists and do not limit the scope of $CB_2$ selective agonists contemplated as part of the invention.

A $CB_2$ agonist is herein defined as a molecule that binds to the CB2 receptor and causes activation of the receptor as measured in one or more assays designed to detect said receptor activation. Such assays can be either in vitro assays or in vivo assays. Typical in vitro assays for measuring $CB_2$ receptor activation include, but are not limited to, the measurement of cyclic AMP accumulation (Mukherjee, *Eur. J. Pharmacol. Vol.* 505, pages 1-9, 2004), the measurement of $Ca^{2+}$ flux using a fluorometric imaging plate reader (Mukherjee, *Eur. J. Pharmacol. Vol.* 505, pages 1-9, 2004), the measurement of GTPγS binding (MacLennan et al., *British J. Pharm. Vol.* 124 pages 619-622, 1998)) and the measurement of ERK or MAP kinase (Yao, *Br. J. Pharmacol. Vol.* 149, pages 145-154, 2006). In vivo assays for detecting $CB_2$ receptor activation include the measurement of activity in a pain model upon administration of a test compound, said activity being reversed by pretreatment with a $CB_2$ selective antagonist or inverse agonist. This protocol is well-known to those skilled in the art and can be found in the following list of references: Clayton, *Pain Vol.* 96, pages 253-260, 2002; Ibrahim, *Proc. Natl. Acad. Sci. Vol.* 100, pages 10529-10533, 2003; LaBuda, *Eur. J. Pharmacol. Vol.* 527, pages 172-174, 2005. Pain models used to detect $CB_2$ receptor activation may be any of those described herein or known to those skilled in the art. As defined herein a $CB_2$ agonist need not show $CB_2$ receptor activation in both an in vitro and in vivo assay but must show activity in at least one in vitro or in vivo assay designed to measure such activity. Under certain artificial assay conditions a $CB_2$ receptor agonist such as AM1241 may appear to not activate the $CB_2$ receptor in vitro (Yao, *Br. J. Pharmacol. Vol.* 149, pages 145-154, 2006) yet it may still activate the $CB_2$ receptor in vivo as measured using one of the in vivo assays described above.

A $CB_2$ agonist may possess varying degrees of selectivity relative to activity at the $CB_1$ receptor as measured in biological assays. A $CB_2$ selective agonist is herein defined as a ligand that binds to or activates the $CB_2$ receptor with at least about 100 times or greater potency than it binds to or activates the $CB_1$ receptor. It is not necessary that a molecule be considered selective in both binding and functional (activation) assays to be a $CB_2$ selective agonist. Binding potency is routinely reported as the Ki, with a lower Ki value equating with greater potency. Thus, a $CB_2$ selective agonist possesses a $CB_2$ binding Ki that is at least about 100 times or more lower than its $CB_1$ binding Ki. Potency to activate a receptor is also routinely reported as the $EC_{50}$, with the lower $EC_{50}$ value equating with a greater potency. The $EC_{50}$ value is also associated with a measured maximum response (efficacy) in an assay relative to a reference standard. CP55,940 is a commonly used reference standard agonist at the $CB_2$ and $CB_1$ receptors, and its maximum response is set at 100%. Test compounds thus may demonstrate full, partial or no substantial efficacy relative to CP55,940. Full efficacy represents a response of greater than or equal to about 70%. Partial efficacy represents a response of approximately 20-70%. Substantially no efficacy represents a response of less than about 20%. Since the $EC_{50}$ value is the approximate concentration that gives a 50% response relative to the maximum for the particular test agent, a test agent with a lower intrinsic efficacy may yield a lower $EC_{50}$ value when compared with an agent that possesses higher intrinsic efficacy. When dealing with test agents that possess substantially different intrinsic efficacies at $CB_2$ and $CB_1$ receptors, establishing the degree of $CB_2$ selectivity may not be possible simply by comparing $EC_{50}$ values, since these each may be based upon substantially different maxima. Thus, a meaningful mathematical calculation of $CB_2$ selectivity cannot be made by comparing the $CB_2$ and CB1 $EC_{50}$s for a representative test agent that potently activates the $CB_2$ receptor with full efficacy and weakly activates the $CB_1$ receptor with no substantial efficacy. Yet such a compound would generally be appreciated by one skilled in the art as a $CB_2$ selective agonist. A $CB_2$ selective agonist, thus, produces a particular degree of activation of the $CB_2$ receptor at a concentration at least about 100 times or more lower than the concentration to elicit substantially the same degree of activation of the $CB_1$ receptor relative to a reference standard agonist like CP55,940. In other words, the concentration to activate the CB2 receptor is at least about 100 times or more lower than the equi-effective concentration to activate the $CB_1$ receptor. The equi-effective concentration refers to the concentration that produces substantially the same degree of activation of the $CB_1$ receptor as the $CB_2$ receptor, wherein this degree of activation could range from 20% to 100%. Also, a compound that partially or fully activates the $CB_2$ receptor and does not substantially activate the $CB_1$ receptor is considered a $CB_2$ selective agonist.

For purposes of the present invention a $CB_2$ selective agonist possesses a $CB_2$ binding Ki of less than or equal to 100 nM, preferably less than or equal to 10 nM, and a selectivity ratio of 100 or greater relative to the $CB_1$ receptor.

The $CB_2$ selective agonist of the present invention also possesses a $CB_2$ binding Ki of less than or equal to 10 nM and a selectivity ratio of 1000 or greater relative to the CB receptor.

For purposes of the invention a $CB_2$ selective agonist possesses a $CB_2$ binding Ki of less than or equal to 1 nM and a selectivity ratio of 100 or greater, preferably 1000, more preferably 10,000, relative to the $CB_1$ receptor.

To determine the selectivity (Ki) of the compounds of the present application for $CB_2$ receptors relative to $CB_1$ receptors, radioligand binding assays are performed, which are described herein.

For $CB_2$ radioligand binding assays, HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands in concentrations selected from the range of 0.01 nM to 10 μM. The addition of 10 μM unlabeled CP-55,940 (Tocris, Ellisville, Mo.) was used to assess nonspecific binding.

For $CB_1$ radioligand binding assay HEK293 human $CB_1$ membranes were purchased from Perkin Elmer. Binding was initiated by the addition of membranes (8-12 μg per well) into wells (Scienceware 96-well DeepWell plate, VWR, West Chester, Pa.) containing [$^3$H]CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding.

The compounds used in the examples of the present application preferably bind to $CB_2$ receptors, therefore are selective ligands for the $CB_2$ receptor, as indicated by the relative values of Ki for each of the receptors: (Z)—N-(5-tert-butyl-3-butylthiazol-2(3H)-ylidene)-5-chloro-2-methoxybenzamide (compound A), a $CB_2$ selective agonist, has a Ki for $CB_2$ receptors of 1.8 nM, and a Ki for $CB_1$ receptors of 3670 nM; (Z)—N-(3-(2-methoxyethyl)-4,5-dimethylthiazol-2(3H)-ylidene)-2,2,3,3-tetramethylcyclopropanecarboxamide (compound B), the other $CB_2$ selective agonist used in the present application, has a Ki for $CB_2$ receptors of 0.6 nM, and a Ki for $CB_1$ receptors or 273 nM.

In terms of effectiveness, it is intended that the $CB_2$ selective agonist of the present invention partially or fully activate the CB2 receptor as defined herein.

In terms of effectiveness, it is intended that the $CB_2$ selective agonist of the present invention possesses a $CB_2$ $EC_{50}$ of less than or equal to 100 nM, preferably 10 nM, and fully activates the $CB_1$ receptor with an $EC_{50}$ of 10,000 nM or greater. Additionally, the $CB_2$ selective agonist of the invention possesses a $CB_2$ $EC_{50}$ of less than or equal to 10 nM and fully activates the $CB_1$ receptor with an $EC_{50}$ of 1,000 nM or greater.

It is intended that the $CB_2$ selective agonist of the invention possesses a $CB_2$ $EC_{50}$ of less than or equal to 1 nM and fully activates the $CB_1$ receptor with an $EC_{50}$ of 100 nM or greater, preferably 1000 nM, more preferably 10,000 nM.

The $CB_2$ selective agonist of the invention also possesses a $CB_2$ $EC_{50}$ of less than or equal to 100 nM and partially activates the $CB_1$ receptor, wherein the equi-effective concentration to activate the $CB_1$ receptor is at least 100 times higher than that to activate the $CB_2$ receptor. Also included in the present invention are $CB_2$ selective agonists that possess a $CB_2$ $EC_{50}$ of less than or equal to 10 nM and that partially activate the $CB_1$ receptor, wherein the equi-effective concentration to activate the $CB_1$ receptor is at least 100 to 1000 times higher than that to activate the $CB_2$ receptor.

In one embodiment of the invention a $CB_2$ selective agonist possesses a $CB_2$ $EC_{50}$ of less than or equal to 1 nM and partially activates the $CB_1$ receptor, wherein the equi-effective concentration to activate the $CB_1$ receptor is at least 100 times, preferably 1,000, more preferably 10,000 higher than that to activate the $CB_2$ receptor. For purposes of the invention a $CB_2$ selective agonist possesses a $CB_2$ $EC_{50}$ of less than or equal to 100 nM, preferably less than or equal to 10 nM, more preferably less than or equal to 1 nM, and does not substantially activate the $CB_1$ receptor in vitro.

For purposes of the present invention a $CB_2$ selective agonist produces a response in an in vivo pain model of 30% or more. Said response may be inhibited by a $CB_2$ antagonist or by a $CB_2$ inverse agonist, but not by a $CB_1$ antagonist or $CB_1$ inverse agonist.

A $CB_1$ selective antagonist or $CB_1$ selective inverse agonist is defined herein as a molecule that inhibits the activation of the $CB_1$ receptor or alternatively reduces the basal level of activity of the $CB_1$ receptor. Assays to detect $CB_1$ antagonist and inverse agonist activity are well-known to those skilled in the art, a list of such assays being found in the following references: Pertwee, *Life Sci. Vol.* 76, pages 1307-1324, 2005; Muccioli, *Curr. Med. Chem. Vol.* 12, pages 1361-1394, 2005.

A $CB_2$ antagonist or $CB_2$ inverse agonist is defined herein as a molecule that inhibits the activation of the CB2 receptor or alternatively reduces the basal level of activity of the $CB_2$ receptor. Assays to detect $CB_2$ antagonist and inverse agonist activity are well-known to those skilled in the art, such assays being found or referred to in the following references: Rinaldi-Carmona, *J. Pharmacol. Exp. Ther*. Vol. 284, pages 644-650, 1998; Muccioli, *Exp. Opin. Ther. Pat*. Vol. 16, pages 1405-1423, 2006; Raitio, *Curr. Med. Chem. Vol.* 12 pages 1217-1237, 2005.

Typical $CB_2$ antagonists/inverse agonists that can be utilized to demonstrate $CB_2$ receptor activation in vivo include SR144528 also known as {N-[(1S)-endo-1,3,3-trimethylbicyclo[2.2.1]heptan-2-yl]-5-(4-chloro-3-methylphenyl)-1-(4-methylbenzyl)-pyrazole-3-carboxamide} and AM630 also known as (6-iodo-2-methyl-1-(2-morpholinoethyl)-1H-indol-3-yl)(4-methoxyphenyl)methanone.

Several methods are available to test the efficacy of compounds in alleviating pain; among them are the Incision Model of Postoperative Pain, Spinal Nerve Ligation Model of Neuropathic Pain, and Capsaicin-induced secondary mechanical hypersensitivity.

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

A skin incision model of postoperative pain was produced using the procedures described in Brennan et al., 1996, Pain, 64, 493. All rats were anesthetized with isoflurane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was typically assessed 30 minutes after compound administration.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure as described in Dixon, W. J., 1980, Efficient analysis of experimental observations, Ann. Rev. Pharmacol. Toxicol., 20, 441. The effect on paw withdrawal latency of test compounds compared to vehicle control represents the ability of the test compound to reduce allodynia. An increase in the paw withdrawal latency represents an anti-allodynic effect (i.e., a decrease in pain).

A model of spinal nerve ligation-induced (SNL model) neuropathic pain was originally described by Kim and Chung (Kim, S. H. and J. M. Chung, *Pain Vol.* 50, page 355, 1992) and can also be used to test the compounds of the present application The left L5 and L6 spinal nerves of the rat are isolated adjacent to the vertebral column and tightly ligated with a 5-0 silk suture distal to the DRG, and care is taken to avoid injury of the L4 spinal nerve. Sham animals undergo the same procedure, but without nerve ligation. All animals are allowed to recover for at least one week and not more than three weeks prior to assessment of tactile allodynia. Only animals with a baseline threshold score of less that 4.25 g are used in this study, and animals demonstrating motor deficit are excluded. Tactile allodynia thresholds are also assessed in several control groups, including naive, sham-operated, and saline infused animals as well as in the contralateral paws of nerve-injured animals.

In the capsaicin-induced secondary mechanical hypersensitivity assay, animals receive capsaicin at 10 μg in 10 μl of vehicle (10% ethanol and 2-hydroxypropyl cyclodextrin) by intraplantar injection into the center of the right hind paw. Secondary mechanical hyperalgesia is measured at the heel away from the site of injection at 180 min following capsaicin (Joshi et al 2006, Neuroscience 143, 587-596). Compounds are injected (i.p.) 30 min before testing (150 min post-capsaicin). Tactile allodynia is measured as described above.

Adverse effects can be assessed by measurements of Grip Force (GF) Behavior. Measurements of hind limb grip force are conducted by recording the maximum compressive force exerted on the hind limb strain gauge setup, in a commercially available grip force measurement system (Columbus Instruments, Columbus, Ohio). During testing, animals are gently restrained by grasping around its rib cage and then allowed to grasp the wire mesh frame (10×12 $cm^2$) attached to the strain gauge. The experimenter then moves the animal in a rostral-to-caudal direction until the grip is broken. Each animal is sequentially tested twice at approximately 2-3 min interval to obtain a raw mean grip force ($CF_{max}$). This raw mean grip force data is in turn converted to a maximum hindlimb compressive force ($CF_{max}$) (gram force)/kg body weight for each animal. A group mean±S.E.M. for $CF_{max}$/kg body weight is calculated. A group of age-matched naïve animals are added to each experiment and the data obtained from the different dose groups for each compound—or compound combination—being tested are compared to the naïve group (assigned as being 100% normal). A reduction in hindlimb grip force for a test compound compared to the effect of vehicle is a measure of adverse effects; the greater the reduction in grip force, the greater the adverse effect. All experiments evaluating drug effects in this model are conducted in a randomized blinded fashion. The statistical analysis of variance (ANOVA) is carried out using GraphPad Prism (GraphPad Software, Inc., San Diego, Calif.). Bonferroni's multiple comparison test is performed as a post hoc comparison.

Adverse effects may also be determined by the Measurement of Locomotor Activity. Spontaneous activity is assessed in an open-field environment (42 (length)×42 (base)×40 cm (height); Piper Plastics, Libertyville, Ill.) situated inside Versamax/Digiscan monitors, each equipped with infrared sensors (AccuScan Instruments, Inc., Columbus, Ohio) in a dimly illuminated test room. Following administration of test compounds or vehicle control, rats are individually placed into the test chambers and horizontal (locomotion) activity is recorded for 30 min. A reduction in horizontal motor activity for a test compound compared to the effect of vehicle is a measure of adverse effects; the greater the reduction in activity, the greater the adverse effect. Data is analyzed by ANOVA followed by Fisher's Protected Least significant difference (PLSD) analysis as a post hoc comparison (JMP statistic database; SAS Institute, Inc., Cary, N.C.). A $p<0.05$ was considered significant.

The principal embodiment of the present application is a method for treating a subject suffering from a condition treatable with a $CB_2$ selective agonist comprising administering a $CB_2$ selective agonist in an amount sufficient to obtain a therapeutic effect in combination with a $CB_1$ antagonist in an amount sufficient to block any residual adverse effect from the $CB_2$ selective agonist but not reduce the therapeutic effect of said $CB_2$ selective agonist. This combination therapy can be effective by separately administering each of the two compounds at the same time or one immediately after the other in doses sufficient to obtain the desired therapeutic effect. This combination therapy can also be effective by combining both compounds in the same pharmaceutical composition in amounts effective to obtain the desired therapeutic effect.

In another embodiment, the present application provides a pharmaceutical composition that comprises the compounds of the present invention. The pharmaceutical compositions comprise compounds of the present invention formulated separately or together with one or more non-toxic pharmaceutically acceptable carriers. The pharmaceutical compositions of this invention can be administered to humans and other mammals orally, rectally, parenterally, intracisternally, intravaginally, topically (as by powders, ointments or drops), bucally or as an oral or nasal spray. The term "parenterally," as used herein, refers to modes of administration that include intravenous, intramuscular, intraperitoneal, intrasternal, subcutaneous and intraarticular injection and infusion.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug(s), it is desirable to slow the absorption of the drug(s) from subcutaneous or intramuscular injection. This can be accomplished by the use of a liquid suspension of crystalline or amorphous material with poor water solubility, or by dissolving or suspending the drug(s) in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissues.

Solid dosage forms for oral administration include capsules, tablets, pills, powders and granules. In such solid dosage forms, the active compound(s) may be mixed with at least one inert, pharmaceutically acceptable carrier or excipient, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions that can be used include polymeric substances and waxes.

The active compound(s) can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Dosage forms for topical administration of a compound of this invention include powders, sprays, ointments and inhalants. The active compound may be mixed under sterile conditions with a pharmaceutically acceptable carrier and any needed preservatives, buffers or propellants, which may be required. Ophthalmic formulations, eye ointments, powders and solutions are also contemplated as being within the scope of this invention.

Actual dosage levels of the active ingredients in the pharmaceutical compositions of this application will depend upon the activity of the particular compound, the route of administration, the severity of the condition being treated and the condition and prior medical history of the patient being treated.

When used in the above or other treatments, a therapeutically effective amount of one of the compounds of the present invention can be employed in pure form or, where such forms exist, in pharmaceutically acceptable salt, ester or prodrug form. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The following examples are only intended to illustrate and not to limit the scope of the present application.

Example 1

$CB_2$ Selective Agonists Effective in Skin Incision Model

Figure 1B:
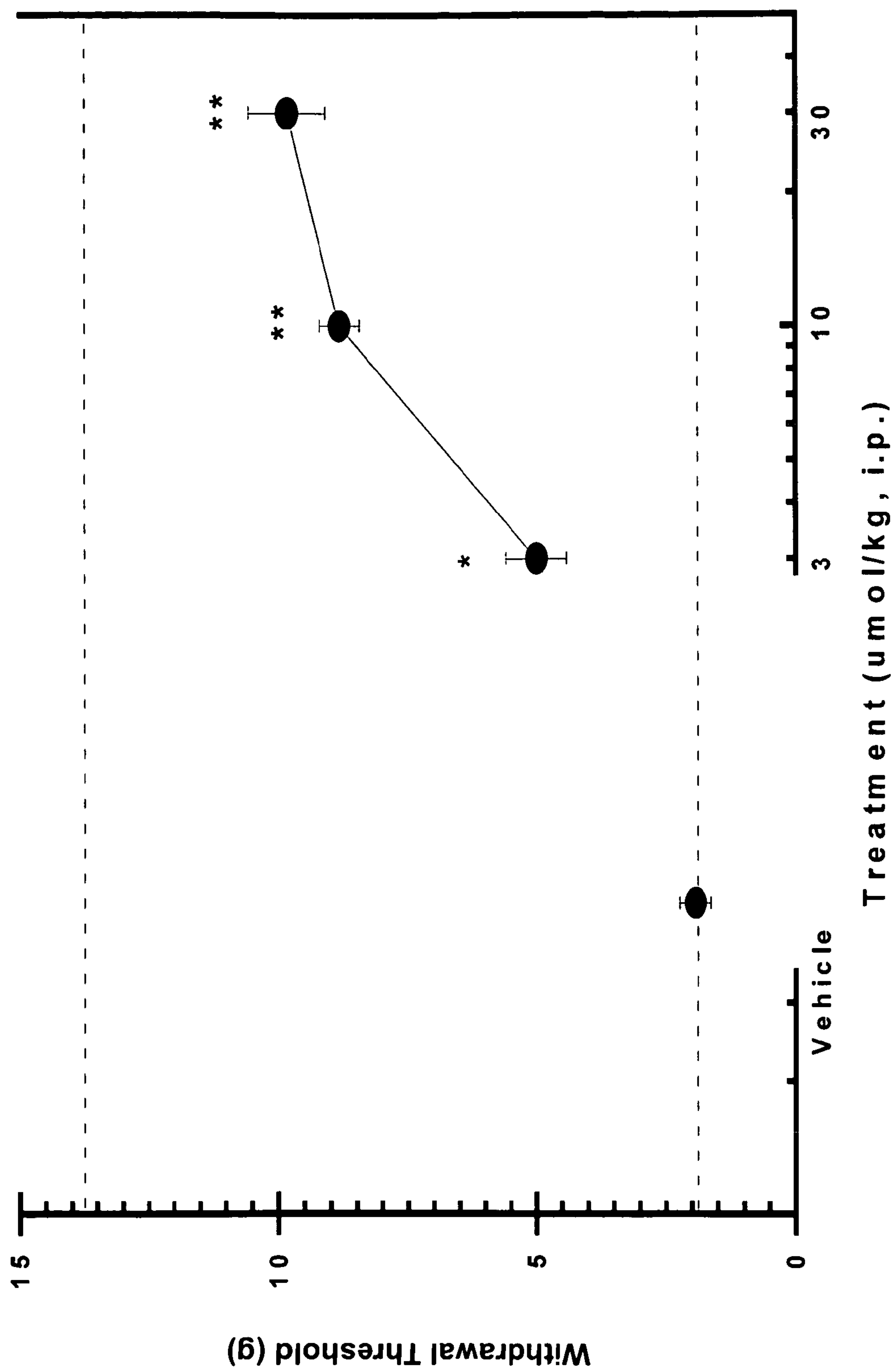
FIG. 1B shows the effect of (Z)—N-(3-(2-methoxyethyl)-4,5-dimethylthiazol-2(3H)-ylidene)-2,2,3,3-tetramethylcyclopropanecarboxamide, a $CB_2$ selective agonist, in skin incision pain model.

Using the skin incisional model of postoperative pain, the effects of compound A, $CB_2$ agonist (Z)—N-(5-tert-butyl-3-butylthiazol-2(3H)-ylidene)-5-chloro-2-methoxybenzamide, on allodynia was assessed two hours after surgery. FIG. 1A shows that the withdrawal threshold for the incisional paw recovered upon i.p. administration of 10 and 30 μmol/kg of $CB_2$ agonist A. FIG. 1B shows similar results with compound B, $CB_2$ agonist (Z)—N-(3-(2-methoxyethyl)-4,5-dimethylthiazol-2(3H)-ylidene)-2,2,3,3-tetramethylcyclopropanecarboxamide, re-establishing withdrawal threshold at 10 and 30 μmol/kg i.p. These results indicate the potent effects obtained with $CB_2$ agonists in this rat pain model.

Example 2

Figure 2:
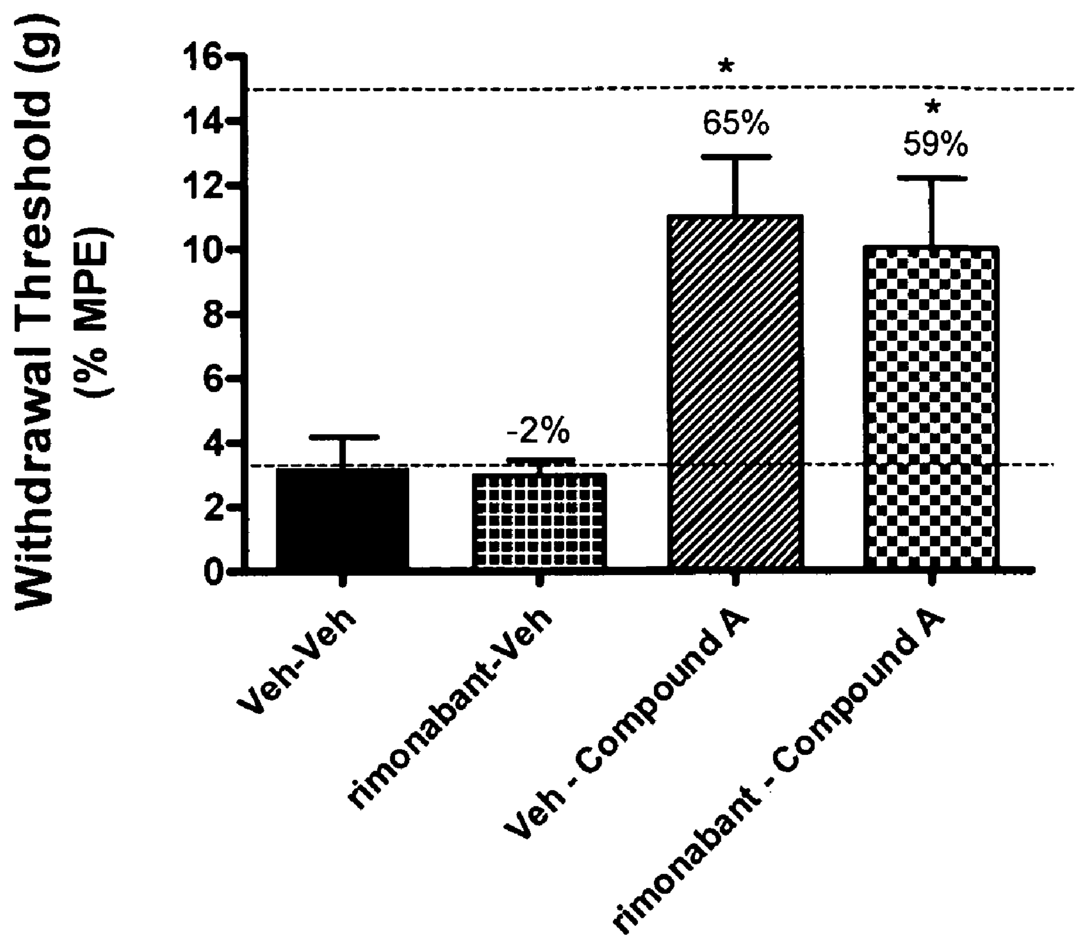
FIG. 2 depicts the effect of co-dosing of (Z)—N-(5-tert-butyl-3-butylthiazol-2(3H)-ylidene)-5-chloro-2-methoxybenzamide (30 μmol/kg, intraperitoneally), a $CB_2$ agonist and rimonabant (30 μmol/kg, intraperitoneally), on skin incision pain model.

Effects of $CB_2$ Agonist and $CB_1$ Antagonist on Analgesia in Skin Incision Model Using the skin incisional model of postoperative pain, the effects of $CB_2$ agonist A were evaluated after the administration of vehicle or the $CB_1$ antagonist rimonabant. This effect was compared with the administration of vehicle after the administration of vehicle or the CB1 antagonist rimonabant. A first dose, consisting of $CB_1$ antagonist rimonabant (30 μmol/kg i.p.) or a vehicle (5% DMSO/PEG), was administered 15 minutes before a second dose, consisting of administration of $CB_2$ agonist A (30 μmol/kg i.p.) or vehicle. Allodynia testing was conducted 30 minutes after administration of the second dose, either CB2 agonist A or vehicle. FIG. 2 shows that either the two administrations of vehicle or the administration of vehicle 15 minutes after the $CB_1$ antagonist rimonabant did not ameliorate the tactile allodynia in the operated rats. FIG. 2 also shows that $CB_2$ agonist A administered after vehicle, or the CB1 antagonist rimonabant, was able to induce analgesia in this model. These results indicate that the level of analgesia induced by the $CB_2$ agonist was not affected by the prior administration of a $CB_1$ antagonist.

Example 3

Figure 3:
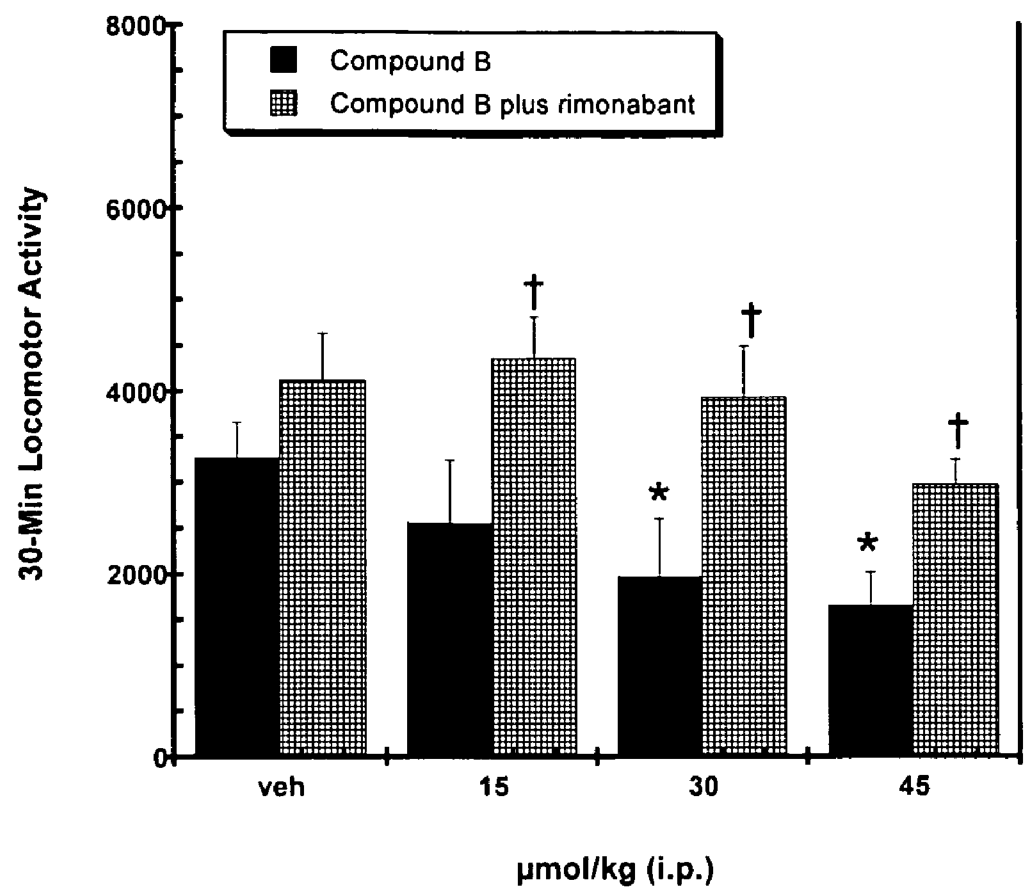
FIG. 3 depicts the effects of co-dosing of (Z)—N-(3-(2-methoxyethyl)-4,5-dimethylthiazol-2(3H)-ylidene)-2,2,3,3-tetramethylcyclopropanecarboxamide (μmol/kg, intraperitoneally), a $CB_2$ selective agonist, and rimonabant (30 μmol/kg, intraperitoneally), on motor activity.

Effects of $CB_1$ Antagonist and $CB_2$ Agonist B on Spontaneous Locomotor Activity FIG. 3 shows that $CB_2$ agonist B significantly reduces spontaneous locomotor activity when administered to rats at 30 and 45 μmol/kg i.p. (solid bars). This reduction in locomotor activity was eliminated when 30 μmol/kg i.p $CB_1$ antagonist rimonabant was administered 15 minutes before the administration of $CB_2$ agonist B. All tests were conducted 30 minutes after the administration of CB2 agonist B. These results indicate that a higher dose of the $CB_2$ agonist B did not reduce the rats' spontaneous activity when administered with a $CB_1$ antagonist. These effects also indicate that the reduction in locomotor activity by CB2 agonist B results from its residual activation of the CB1 receptor. Accordingly, co-dosing $CB_2$ agonist B with the $CB_1$ antagonist rimonabant significantly reduced the adverse effects.

Example 4

Figure 4:
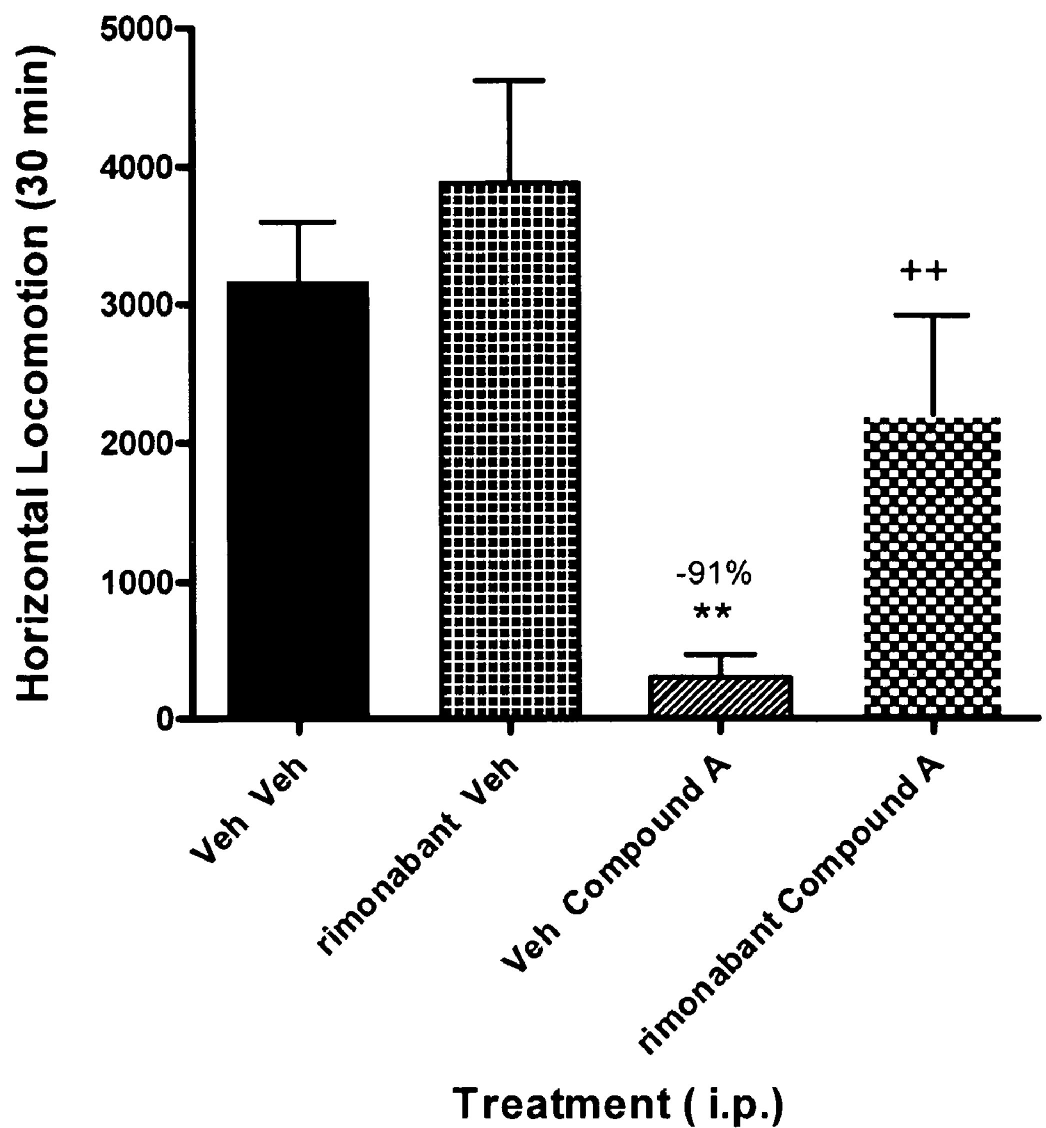
FIG. 4 represents the effects of co-dosing (Z)—N-(5-tert-butyl-3-butylthiazol-2(3H)-ylidene)-5-chloro-2-methoxybenzamide, a $CB_2$ selective agonist (30 μmol/kg, intraperitoneally), and rimonabant (30 μmol/kg, intraperitoneally) on motor activity.

Effects of $CB_1$ Antagonist and $CB_2$ Agonist A on Spontaneous Locomotor Activity Using the locomotor activity assay, the effects of $CB_2$ agonist A were evaluated after the administration of vehicle or the $CB_1$ antagonist rimonabant. This effect was compared with the administration of vehicle after the administration of vehicle or the CB1 antagonist rimonabant. A first dose, consisting of $CB_1$ antagonist rimonabant (30 μmol/kg i.p.) or a vehicle (5% DMSO/PEG), was administered 15 minutes before a second dose, consisting of administration of $CB_2$ agonist A (30 μmol/kg i.p.) or vehicle. Locomotor testing was conducted 30 minutes after administration of the second dose, either CB2 agonist A or vehicle. FIG. 4 shows that $CB_1$ antagonist rimonabant did not affect horizontal locomotor activity of vehicle. $CB_2$ agonist A administered after vehicle decreased horizontal locomotor activity by 91%. $CB_1$ antagonist rimonabant was able to block said decrease when administered 15 minutes prior to $CB_2$ agonist A. These effects indicate that the reduction in locomotor activity by CB2 agonist A results from its residual activation of the CB1 receptor. FIG. 4 shows that administration of $CB_1$ antagonist and $CB_2$ agonist eliminates unwanted side effects induced by residual $CB_1$ activity of the $CB_2$ agonist.

Example 5

Effect of $CB_1$ Antagonist and $CB_2$ Agonist on Grip Force Behavior

Figure 5:
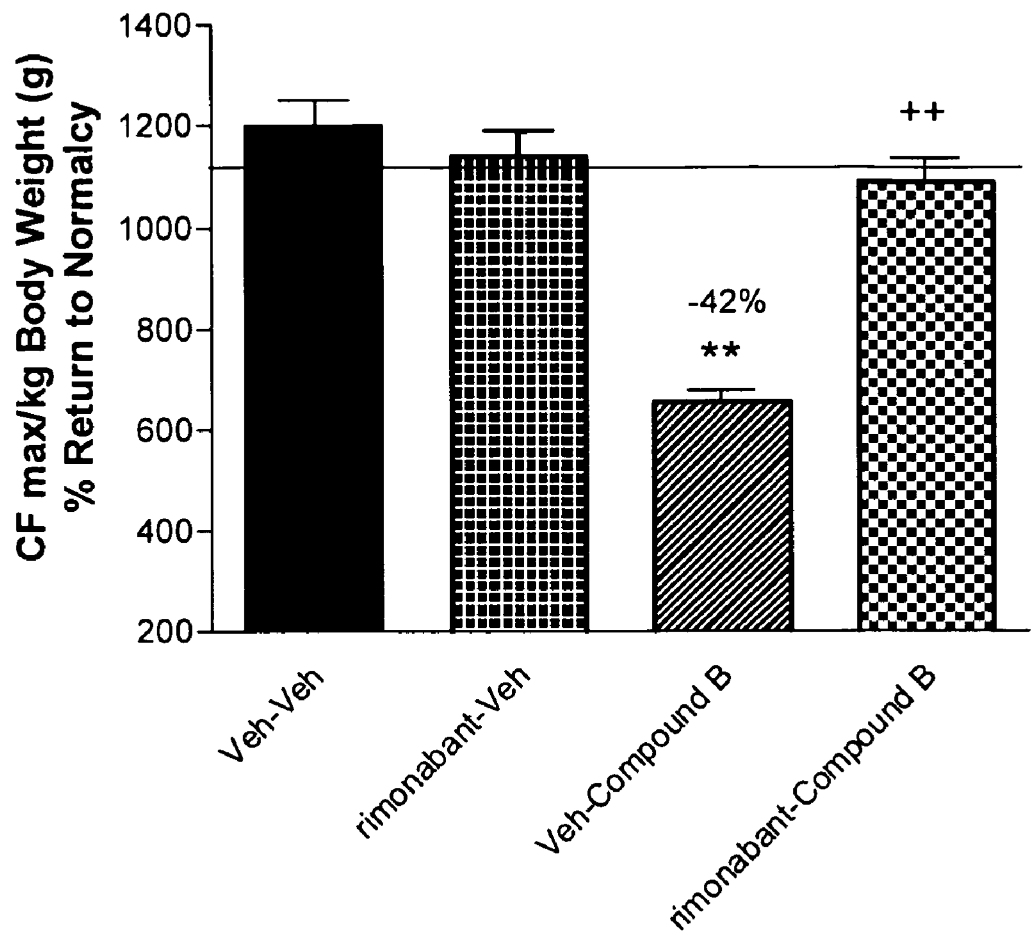
FIG. 5 summarizes the effects of co-dosing of (Z)—N-(3-(2-methoxyethyl)-4,5-dimethylthiazol-2(3H)-ylidene)-2,2,3,3-tetramethylcyclopropanecarboxamide (30 μmol/kg, intraperitoneally), a $CB_2$ selective agonist, and rimonabant (30 μmol/kg, intraperitoneally), on grip force.

Using the grip force behavior assay, the effects of $CB_2$ agonist B were evaluated after the administration of vehicle or the $CB_1$ antagonist rimonabant. This effect was compared with the administration of vehicle after the administration of vehicle or the CB1 antagonist rimonabant. A first dose, consisting of $CB_1$ antagonist rimonabant (30 μmol/kg i.p.) or a vehicle (5% DMSO/PEG), was administered 15 minutes before a second dose, consisting of administration of $CB_2$ agonist B (30 μmol/kg i.p.) or vehicle. Grip force behavior testing was conducted 30 minutes after administration of the second dose, either CB2 agonist B or vehicle. FIG. 5 shows $CB_2$ agonist B induced reduction of grip force by 42% (30 μmol/kg i.p). This effect was completely blocked by prior administration of $CB_1$ antagonist rimonabant. As shown in FIG. 5, rimonabant had no effect on the grip force when administered prior to vehicle. These effects indicate that the reduction in grip force by CB2 agonist B results from its residual activation of the CB1 receptor. FIG. 5 shows that administration of $CB_1$ antagonist and $CB_2$ agonist eliminates unwanted side effects induced by residual $CB_1$ activity of the $CB_2$ agonist.

Example 6

Effect of $CB_1$ Antagonist and $CB_2$ Agonist Co-Administration on Mean Arterial Pressure (MAP) and Heart Rate (HR)

Figure 6:
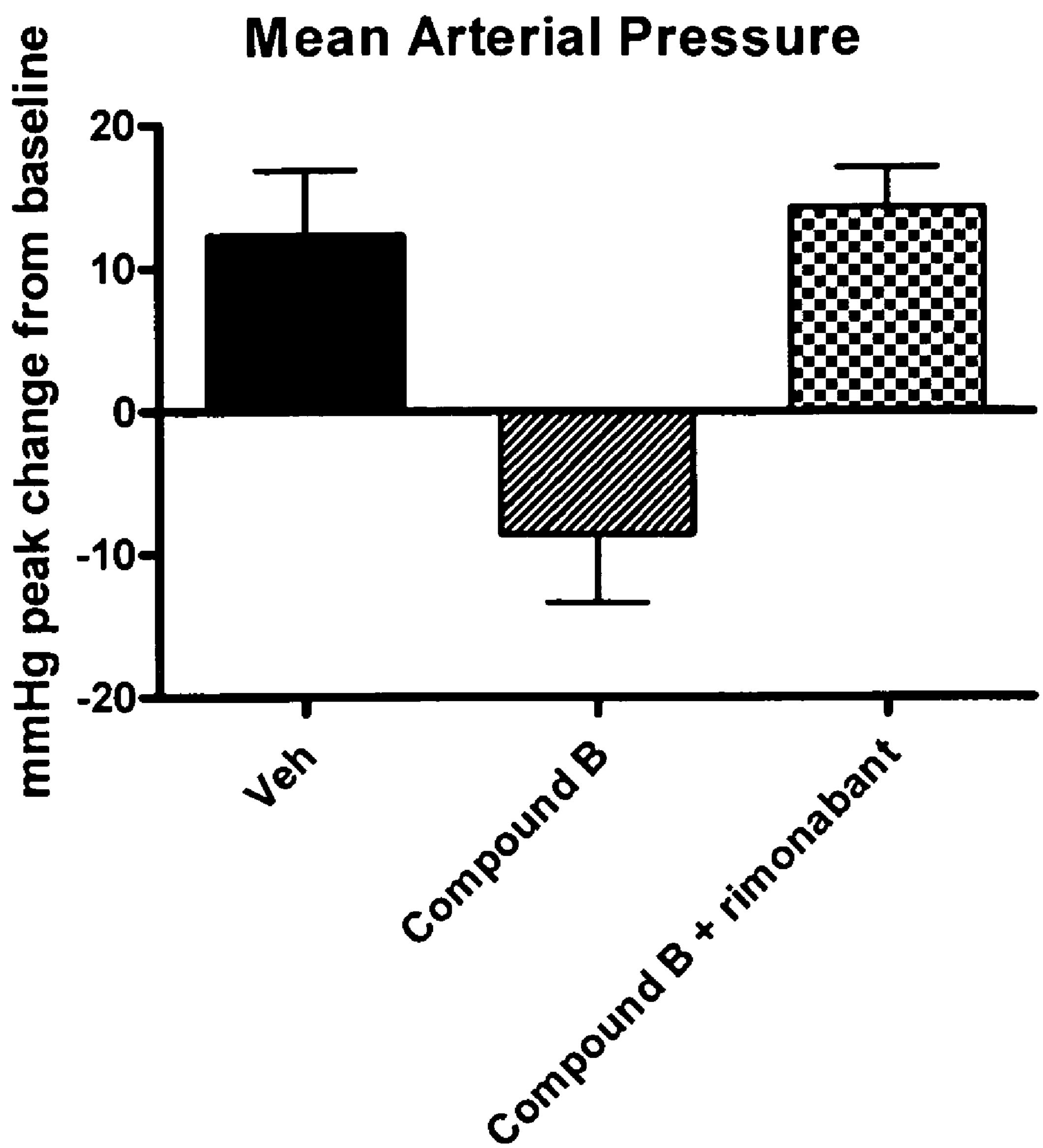
FIG. 6 shows the effects on mean arterial pressure after co-dosing of (Z)—N-(3-(2-methoxyethyl)-4,5-dimethylthiazol-2(3H)-ylidene)-2,2,3,3-tetramethylcyclopropanecarboxamide (1 mg/kg, intravenously), a $CB_2$ selective agonist, and rimonabant (3.2 mg/kg, intravenously).

Male Sprague-Dawley rats were anesthetized with the long acting barbiturate, Inactin. Catheters were placed in the femoral artery for measurement of MAP and HR. Additional catheters were placed in the femoral vein for compound administration and saline infusion to maintain hydration. Following a 30-minute control period, vehicle (PEG400), compound B (vehicle: PEG400; 2 ml/kg) or $CB_2$ agonist B (vehicle: PEG400; 2 ml/kg) plus $CB_1$ antagonist rimonabant (vehicle: PEG400; 1 ml/kg) was administered intravenously over a 30-minute infusion. When administered simultaneously, compound B and rimonabant were infused individually using separate syringes. The doses tested were 1.0 mg/kg for compound B and 3.2 mg/kg for rimonabant. Data is expressed as mean from 3 rats ±sem. FIG. 6 demonstrates the effects on mean arterial pressure (MAP) of administration of vehicle, compound B alone, and compound B with rimonabant. These results demonstrate that the combination treatment of compound B with rimonabant is devoid of an effect on blood pressure relative to vehicle whereas the treatment with compound B has an effect to reduce blood pressure. These effects indicate that the reduction in blood pressure by CB2 agonist B results from its residual activation of the CB1 receptor. FIG. 6 shows that administration of $CB_1$ antagonist and $CB_2$ agonist eliminates unwanted side effects induced by residual $CB_1$ activity of the $CB_2$ agonist.

Example 7

Figure 7:
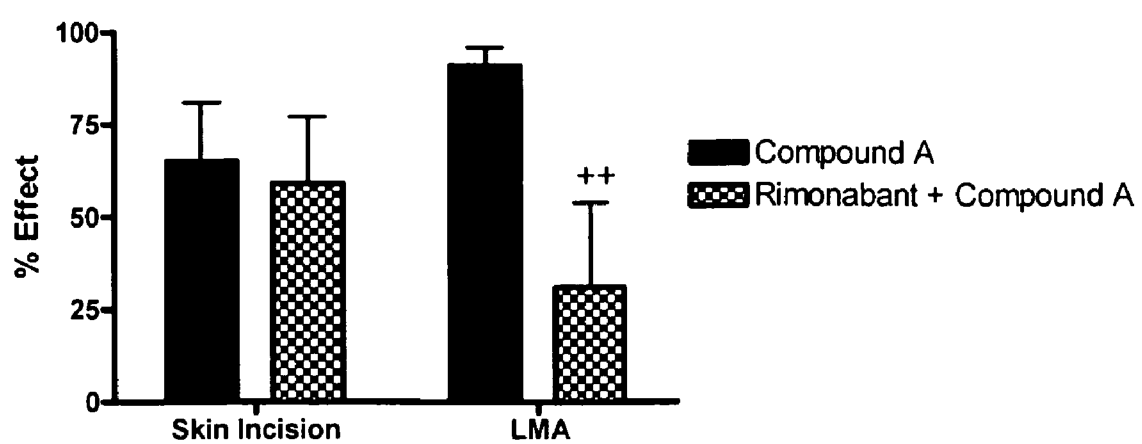
FIG. 7 shows the comparison of efficacy and side effects of (Z)—N-(5-tert-butyl-3-butylthiazol-2(3H)-ylidene)-5-chloro-2-methoxybenzamide, a $CB_2$ selective agonist, alone and in combination with rimonabant. Skin incision refers to the postoperative skin incision pain model. LMA refers to locomotor activity model.

A Comparison of the Efficacy and Side Effects for a $CB_2$ Agonist Alone and a $CB_2$ Agonist dosed with a $CB_1$ Antagonist FIG. 7 shows the effect in the skin incision pain model and the locomotor side effect assay for $CB_2$ agonist compound A, and compound A plus $CB_1$ antagonist rimonabant with the data expressed as the maximum possible effect obtainable in these assays. Compound A and compound A co-dosed with rimonabant show equivalent efficacy in the skin incision pain model. Compound A plus rimonabant shows much reduced side effects in the locomotor assay compared with compound A dosed alone. Compound A was administered at a dose of 30 μmol/kg i.p and rimonabant was administered at a dose of 30 μmol/kg i.p. 15 minutes before compound A.

What is claimed is:

1. A method for treating a subject suffering from pain using a combination therapy comprising administering a selective $CB_2$ receptor agonist selected from the group consisting of (Z)—N-(5-tert-butyl-3-butylthiazol-2(3H)-ylidene)-5-chloro-2-methoxybenzamide and (Z)—N-(3-(2-methoxyethyl)-4,5-dimethylthiazol-2(3H)-ylidene)-2,2,3,3-tetramethylcyclopropanecarboxamide in an amount effective to obtain a therapeutic effect, and rimonabant in an amount effective to block any adverse effects mediated by the $CB_1$ receptor, but not to antagonize the therapeutic effect of the $CB_2$ receptor agonist.

2. The method of claim 1 wherein the pain is selected from the group comprising neuropathic pain, nociceptive pain, and inflammatory pain.

3. The combination therapy of claim 1, wherein the $CB_2$ receptor agonist and the rimonabant are administered as separate pharmaceutical compositions including a pharmaceutically acceptable carrier.

4. The combination therapy of claim 1, wherein the $CB_2$ receptor agonist and the rimonabant are administered together as one pharmaceutical composition including a pharmaceutically acceptable carrier.

5. A composition comprising a selective $CB_2$ receptor agonist selected from the group consisting of (Z)—N-(5-tert-butyl-3-butylthiazol-2(3H)-ylidene)-5-chloro-2-methoxybenzamide and (Z)—N-(3-(2-methoxyethyl)-4,5-dimethylthiazol-2(3H)-ylidene)-2,2,3,3-tetramethylcyclopropanecarboxamide in an amount effective to produce a therapeutic effect, rimonabant in an amount effective to antagonize side and adverse effects produced by the $CB_2$ agonist, but not to antagonize the therapeutic effect of the $CB_2$ agonist, and a pharmaceutically acceptable carrier.

* * * * *